(12) United States Patent
Westwick et al.

(10) Patent No.: US 12,015,858 B2
(45) Date of Patent: Jun. 18, 2024

(54) SYSTEMS AND METHODS OF DUAL FLUOROPHORE RATIOMETRIC IMAGING

(71) Applicant: Stryker Corporation, Kalamazoo, MI (US)

(72) Inventors: Paul Roald Westwick, Vancouver (CA); Frederick Allen Moore, Vancouver (CA)

(73) Assignee: Stryker Corporation, Kalamazoo, MI (US)

( * ) Notice: Subject to any disclaimer, the term of this patent is extended or adjusted under 35 U.S.C. 154(b) by 186 days.

(21) Appl. No.: 17/561,671

(22) Filed: Dec. 23, 2021

(65) Prior Publication Data

US 2022/0210379 A1    Jun. 30, 2022

Related U.S. Application Data

(60) Provisional application No. 63/132,450, filed on Dec. 30, 2020.

(51) Int. Cl.
*H04N 25/13* (2023.01)
*A61B 5/00* (2006.01)

(52) U.S. Cl.
CPC ......... *H04N 25/134* (2023.01); *A61B 5/0071* (2013.01)

(58) Field of Classification Search
None
See application file for complete search history.

(56) References Cited

U.S. PATENT DOCUMENTS

| | | | |
|---|---|---|---|
| 2012/0230918 A1* | 9/2012 | Dobosz | G01N 21/6428 424/9.6 |
| 2014/0276008 A1* | 9/2014 | Steinbach | A61B 5/0059 600/424 |
| 2017/0245766 A1 | 8/2017 | Flower | |
| 2017/0354392 A1 | 12/2017 | Fengler | |
| 2019/0041333 A1* | 2/2019 | Doser | A61B 5/0071 |
| 2020/0146564 A1 | 5/2020 | Lund | |
| 2020/0150041 A1* | 5/2020 | Harootunian | G01N 21/6456 |

OTHER PUBLICATIONS

International Preliminary Report on Patentability dated Jul. 4, 2023, directed to International Application No. PCT/US2021/073104; 7 pages.
International Search Report and Written Opinion dated Apr. 20, 2022, directed to International Application No. PCT/US2021/073104; 11 pages.

* cited by examiner

*Primary Examiner* — Katherine L Fernandez
(74) *Attorney, Agent, or Firm* — Morrison & Foerster LLP

(57) ABSTRACT

Methods and systems of distinguishing between fluorescence imaging data contributions corresponding to two fluorescence imaging agents in a tissue is described herein. Specifically, exploitation of an imaging sensor with a color filter array can help distinguish between overlapping simultaneous fluorophore emission profiles.

10 Claims, 5 Drawing Sheets

SYSTEMS AND METHODS OF DUAL FLUOROPHORE RATIOMETRIC IMAGING

CROSS-REFERENCE TO RELATED APPLICATIONS

This application claims the benefit of U.S. Provisional Application No. 63/132,450, filed Dec. 30, 2020, the entire contents of which are hereby incorporated by reference herein.

FIELD

The present disclosure relates generally to medical imaging, and more particularly to fluorescence imaging for visualizing blood flow in tissue of a subject.

BACKGROUND

Medical imaging systems (e.g., endoscopic imaging systems for minimally invasive surgery or open field medical imaging systems) can help provide clinical information to medical practitioners making decisions (e.g. intraoperative or treatment decisions) based on attributes of tissue of a subject. In many instances, it is useful for medical imaging systems to provide fluorescence imaging for visualizing tissue or attributes of tissue that cannot be visualized or are poorly visualized with white light imaging. Fluorescence imaging generally involves the administration of a bolus of a fluorescence imaging agent that is present in the subject's tissue and emits a fluorescence signal when illuminated with the appropriate excitation light. However, there may be situations in which two different imaging agents are utilized.

A fluorescence imaging system can acquire images of the fluorescence signal emitted by the imaging agent(s) as the bolus passes through or localizes in the subject's tissue in the imaging field of view. The fluorescence images may be used to make qualitative or quantitative assessments of attributes of the tissue under observation.

SUMMARY

According to various aspects, systems and methods disclosed herein can enable imaging of two bands of fluorescence with a single image sensor with a color filter array. Utilizing an image sensor with a color filter array (e.g., Bayer filter sensor) can help distinguish between overlapping simultaneous fluorescence imaging agent (e.g., Cy5 and Cy7 from Avelas) emission profiles. In some aspects, the fluorescence emission response of each color channel of a color filter array sensor to different fluorescence bands can be calculated. This can be calculated by integrating the product of the fluorescence emission profile at each wavelength and sensor color channel response at that wavelength. Based on known color channel responses, images of a combination of fluorophore emissions can be decoupled by solving a system of equations.

In some aspects, the methods and systems disclosed herein can be used to image two bands of NIR fluorescence with a single Bayer-pattern image sensor. In some aspects, the two bands of NIR fluorescence can be imaged by a single-chip camera technology, either endoscopic or open-field.

According to various aspects, a method for distinguishing between fluorescence imaging data contributions corresponding to two fluorescence imaging agents in a tissue of a patient during surgical imaging, comprises: illuminating the tissue with excitation light to simultaneously excite both a first fluorescence imaging agent and a second fluorescence imaging agent in the tissue, wherein the first and second fluorescence imaging agents have different fluorescence emission profiles in the tissue; receiving fluorescence imaging data of the tissue illuminated by the excitation light from an imaging sensor with a color filter array, wherein the fluorescence imaging data comprises at least a first pixel value from the sensor corresponding to a first color of the color filter array and a second pixel value from the sensor corresponding to a second color of the color filter array; determining a first contribution to the fluorescence imaging data corresponding to the first fluorescence imaging agent using the first and second pixel values in a first predetermined linear combination; and determining a second contribution to the fluorescence imaging data corresponding to the second fluorescence imaging agent using the first and second pixel values in a second predetermined linear combination, wherein the first and second predetermined linear combinations are based on areas under color response curves of the first fluorescence imaging agent for the first and second colors and color response curves of the second fluorescence imaging agent for the first and second colors, and each of the respective imaging agent color response curves are based on multiplying the respective imaging agent emission profile with a spectral sensitivity of the imaging sensor for the respective color.

Optionally, the color filter array comprises a Bayer filter.

Optionally, the fluorescence imaging data comprises near-infrared fluorescence imaging data.

Optionally, the first and second colors of the color filter array are two selected from the group of red, green, and blue.

Optionally, the first color is red and the second color is green.

Optionally, the first fluorescence imaging agent is Cy5 and the second fluorescence imaging agent is Cy7.

Optionally, the method includes displaying the fluorescence imaging data.

Optionally, the method includes displaying a fluorescence image based on the fluorescence imaging data.

Optionally, the method includes displaying the first contribution to the fluorescence imaging data corresponding to the first fluorescence imaging agent and/or the second contribution to the fluorescence imaging data corresponding to the second fluorescence imaging agent.

Optionally, the method includes displaying a fluorescence image(s) based on the first contribution to the fluorescence imaging data corresponding to the first fluorescence imaging agent and/or the second contribution to the fluorescence imaging data corresponding to the second fluorescence imaging agent.

Optionally, the first contribution and/or the second contribution are displayed using distinct color maps.

Optionally, the method includes subtracting out light such that the only source of light reaching the imaging sensor is fluorescence light from the first and/or second fluorescence imaging agent.

According to various aspects, a non-transitory computer readable storage medium stores one or more programs for execution by one or more processors of a fluorescence imaging system, the one or more programs comprising instructions for performing any of the methods described above. According to an aspect is provided a computer program product comprising instructions which, when executed by one or more processors of a fluorescence imaging system, cause the fluorescence imaging system to perform any of the methods described above.

According to various aspects, a system for fluorescence imaging includes one or more processors, memory, and one or more programs, wherein the one or more programs are stored in the memory and configured to be executed by the one or more processors, the one or more programs including instructions for performing any of the methods described above.

It will be appreciated that any of the variations, aspects, examples, features and options described in view of the methods apply equally to the systems and storage mediums and vice versa. It will also be clear that any one or more of the above variations, aspects, features and options can be combined.

Additional advantages will be readily apparent to those skilled in the art from the following detailed description. The examples, aspects, and descriptions herein are to be regarded as illustrative in nature and not restrictive.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

BRIEF DESCRIPTION OF THE FIGURES

The invention will now be described, by way of example only, with reference to the accompanying drawings, in which.

DETAILED DESCRIPTION

Figure 1:
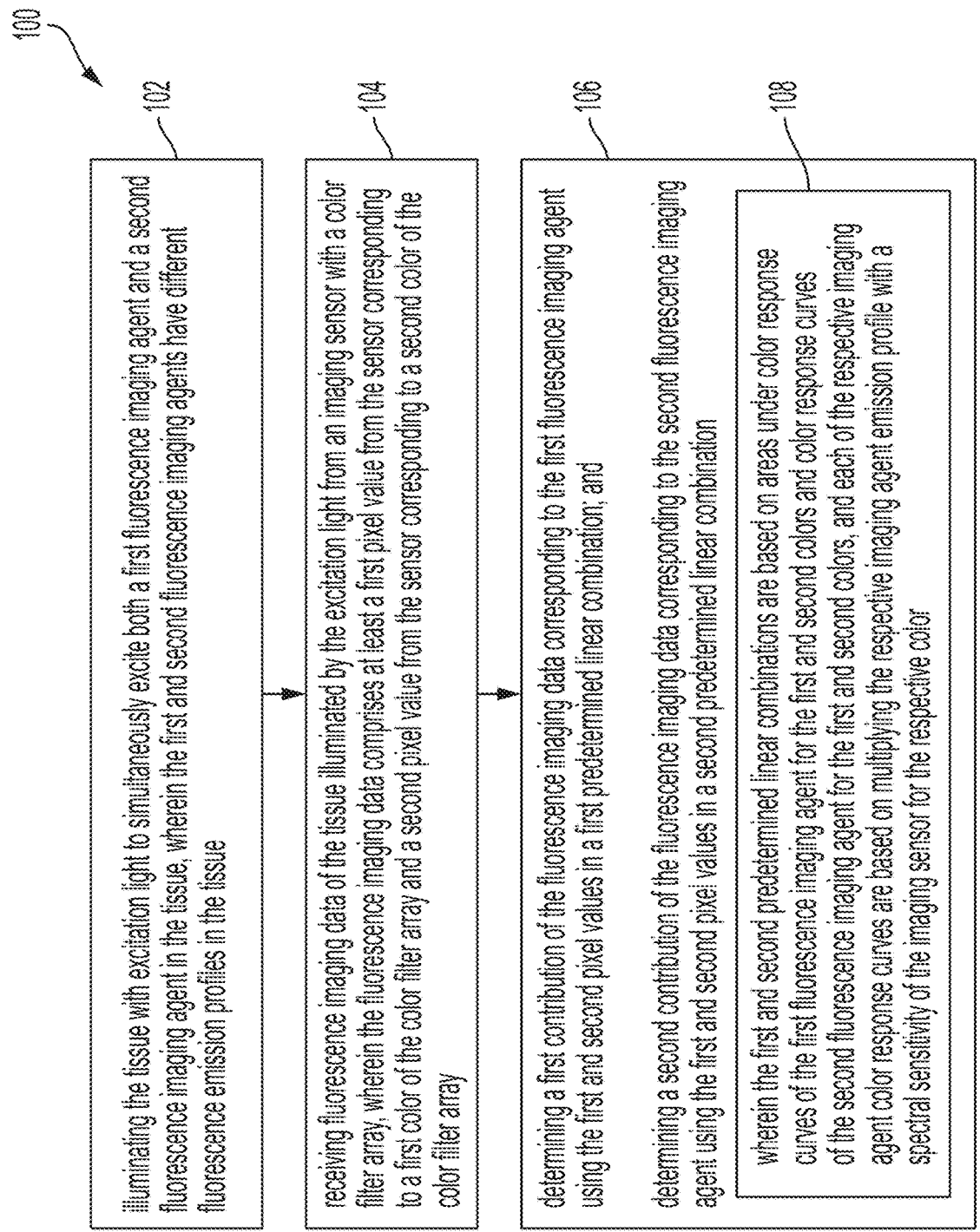
FIG. 1 is a flow diagram for distinguishing between fluorescence image data contributions corresponding to two fluorescence imaging agents in a tissue of a patient during surgical imaging, according to some examples disclosed herein.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein are systems and methods according to various examples for distinguishing between fluorescence imaging data contributions corresponding to two fluorescence imaging agents in a tissue of a patient, which can help a clinician image two imaging agents in tissue with existing camera technology (e.g., endoscopic or open-field). As such, the systems and methods can decouple a combination of fluorescence imaging agent image data in order for the clinician to distinguish between overlapping simultaneous fluorophore emission profiles in a tissue of a patient.

In the following description of the various examples, reference is made to the accompanying drawings, in which are shown, by way of illustration, specific examples that can be practiced. It is to be understood that other examples can be practiced, and changes can be made without departing from the scope of the disclosure.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates a method 100 for distinguishing between fluorescence imaging data contributions corresponding to two fluorescence imaging agents in a tissue of a patient. The method 100 can be performed during surgical imaging. In some examples, surgical imaging can be performed during surgery. Surgical imaging can include situations where the tissue of the patient being imaged may comprise a tissue sample removed from the patient and imaged on a back table during the surgical imaging session. Method 100 is performed based on fluorescence imaging data generated by a fluorescence imaging system and can be performed by the fluorescence imaging system or any computing system communicatively coupled to a fluorescence imaging system that receives fluorescence imaging data from the fluorescence imaging system.

Method 100 may be performed by an imaging system, such as an imaging system that includes an imager for generating fluorescence images and one or more processors for processing the images according to method 100. In some examples, method 100 is performed by an image processing system that receives one or more images from an imaging system and/or from a memory in which one or more images are stored.

Method 100 can be performed after the administration of a bolus of a fluorescence imaging agent or multiple fluorescence imaging agents to a patient and based on fluorescence imaging data generated using a fluorescence imager that has tissue of interest of a subject within its field of view. Depending on the procedure, the tissue of interest can be imaged during an invasive procedure, such as a minimally invasive procedure using an endoscopic imager or an open procedure using an open-field imager, or via a non-invasive procedure, such as involving through-the-skin imaging. The endoscopic imager can be pre-inserted in the patient before performing the method 100.

Figure 2:
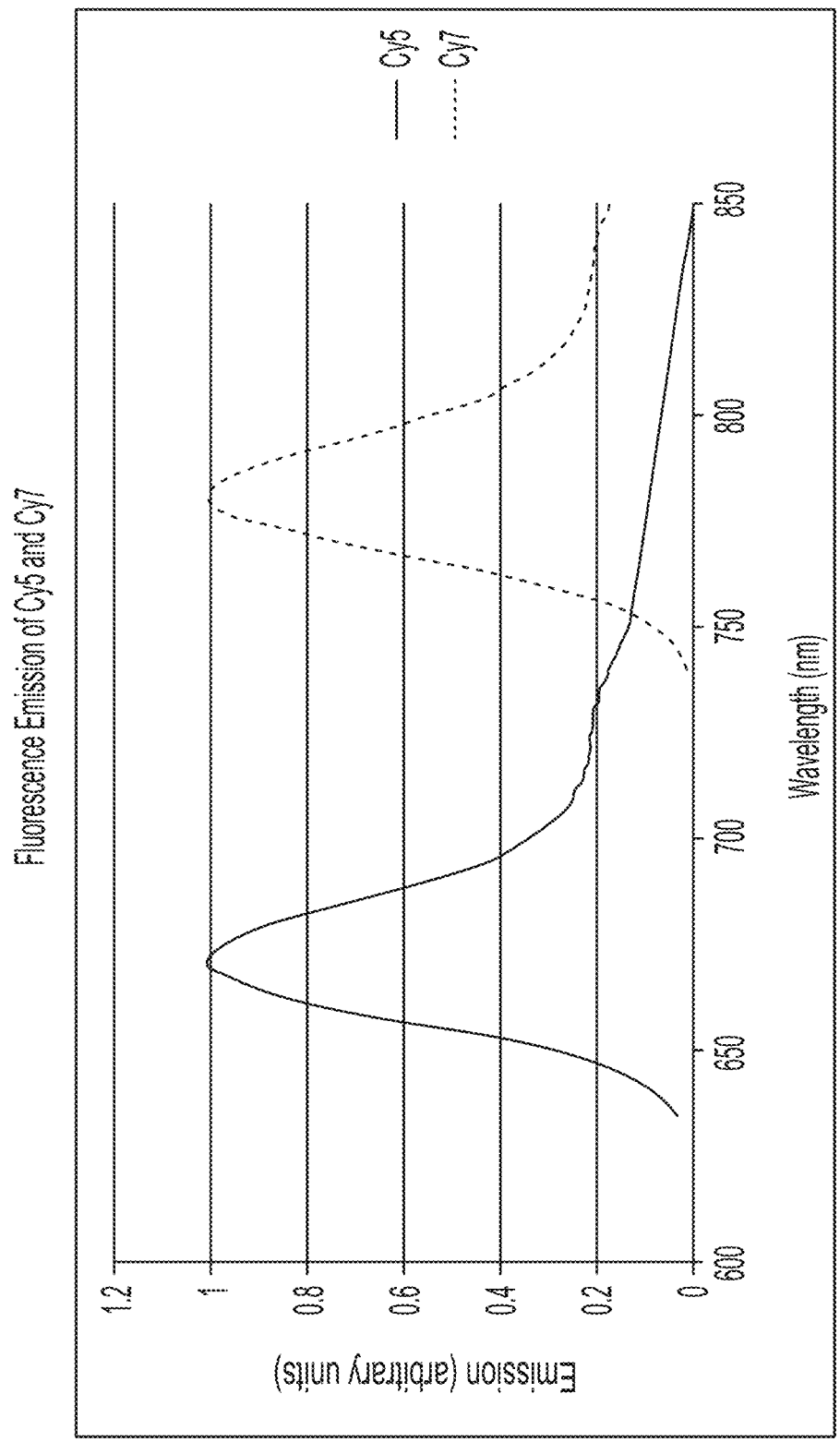
FIG. 2 illustrates fluorescence emission profiles of Cy5 and Cy7 across various wavelengths, according to some examples disclosed herein.

At step 102, tissue containing a first fluorescence imaging agent and a second fluorescence imaging agent can be illuminated with excitation light to simultaneously excite both the first fluorescence imaging agent and the second fluorescence imaging agent in the tissue. The first and second fluorescence imaging agents can have different fluorescence emission profiles in the tissue. For example, FIG. 2 illustrates the fluorescence emission profiles of Cy5 (i.e., a first fluorescence imaging agent) and Cy7 (e.g., a second fluorescence imaging agent) across various wavelengths. As shown in FIG. 2, the emission peak of Cy5 is around 670 nm, while the emission peak of Cy7 is around 780 nm.

In some variations, a suitable fluorescence agent is an agent which can circulate with the blood (e.g., an agent which can circulate with, for example, a component of the blood such as plasma in the blood) and which fluoresces when exposed to appropriate excitation light energy. For example, ICG, when administered to the subject, binds with blood proteins and circulates with the blood in the tissue. The fluorescence imaging agent (e.g., Cy5, Cy7, ICG) may be administered to the subject as a bolus injection (e.g., into a vein or an artery) in a concentration suitable for imaging such that the bolus circulates in the vasculature and traverses the microvasculature. In other aspects in which multiple fluorescence imaging agents are used, such agents may be administered simultaneously, e.g. in a single bolus, or sequentially in separate boluses. In some aspects, the fluorescence imaging agent(s) may be administered by a catheter. The fluorescence imaging agent(s) may be administered in advance of performing the measurement of signal intensity arising from the fluorescence imaging agent(s). In some aspects, the fluorescence imaging agent(s) may be administered several hours (e.g., about 6 hours or about 12 hours) in advance of performing the measurement of signal intensity arising from the fluorescence imaging agent(s). In certain aspects, the fluorescence imaging agent(s) may be administered less than an hour in advance of performing the measurement of signal intensity arising from the fluorescence imaging agent(s). For example, the fluorescence imaging agent(s) may be administered to the subject less than 30 minutes in advance of the measurement. In yet other aspects, the fluorescence imaging agent(s) may be administered at least 30 seconds in advance of performing the measurement. In still other aspects, the fluorescence imaging agent(s) may be administered contemporaneously with performing the measurement. According to some aspects, the fluorescence imaging agent(s) may be administered in various concentrations to achieve a desired circulating concentration in the blood. In various aspects, the upper concentration limit for the administration of the fluorescence imaging agent(s) is the concentration at which the fluorescence imaging agent(s) becomes clinically toxic in circulating blood, and the lower concentration limit is the instrumental limit for acquiring the signal intensity data arising from the fluorescence imaging agent(s) circulating with blood to detect the fluorescence imaging agent(s). In various other aspects, the upper concentration limit for the administration of the fluorescence imaging agent(s) is the concentration at which the fluorescence imaging agent becomes self-quenching. According to some aspects, the fluorescence imaging agent(s) may be administered locally to a region of tissue of the subject. Thus, in one aspect, the method comprises the step of administration of the imaging agents (e.g., fluorescence imaging agents) to the subject and acquisition of the signal intensity data (e.g., video) prior to processing the signal intensity data according to the various aspects. In another aspect, the method excludes any step of administering the imaging agents to the subject.

According to some aspects, suitable fluorescence imaging agents for use in fluorescence imaging applications to generate fluorescence image data are imaging agents which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agents are exposed to appropriate light energy (e.g., excitation light energy, or absorption light energy). In various aspects, the fluorescence imaging agents comprise a fluorescence dye, an analogue thereof, a derivative thereof, or a combination of these. An example of the fluorescence agent is a fluorescence dye, which includes any non-toxic fluorescence dye. In certain variations, the fluorescence dye may include a dye that emits light in the near-infrared spectrum. In certain aspects, the fluorescence dye may include a tricarbocyanine dye such as, for example, indocyanine green (ICG). In other variations, the fluorescence dye may comprise methylene blue, ICG or a combination thereof. In certain aspects the dye is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy3, Cy3.5, Cy5, Cy5.5, Cy7, and Cy7.5, etc.), IRDye800CW, CLR 1502 combined with a targeting ligand, OTL38 combined with a targeting ligand, or a combination thereof, which is excitable using excitation light wavelengths appropriate to each imaging agent(s). In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the targeted and/or background fluorescence is derived from autofluorescence, one or more of the fluorophores or agents giving rise to the autofluorescence may be an endogenous tissue fluorophore (e.g., collagen, elastin, NADH, etc.), 5-aminolevulinic acid (5-ALA) or a derivative or product thereof, or a combination thereof. For example, 5-ALA may be converted in vivo to a product protoporphyrin IX which may emit fluorescence that may be imaged by the fluorescence imager. In some aspects, the first fluorescence imaging agent is Cy5 and the second fluorescence imaging agent is Cy7. In some aspects, the first and second fluorescence imaging agents can be any fluorophors with emission profiles at least partially comprising wavelengths in the NIR, provided they have significantly different response to different filters in the Bayer-pattern sensor.

In various aspects, the fluorescence imaging agent(s) may be provided as a lyophilized powder, solid, or liquid. In certain aspects, the fluorescence imaging agent(s) may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent(s) may be reconstituted with an aqueous diluent immediately before administration. In various aspects, any diluent or carrier which will maintain the fluorescence imaging agent in solution may be used. As an example, ICG may be reconstituted with water. In some aspects, once the fluorescence imaging agent is reconstituted, it may be mixed with additional diluents and carriers. In some aspects, the fluorescence imaging agent(s) may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although fluorescence imaging agents were described above in detail, other imaging agents may be used in connection with the systems, methods, and techniques described herein, depending on the medical imaging modality.

In some variations, the fluorescence imaging agent(s) used in combination with the methods, systems and kits described herein may be used for blood flow imaging, tissue perfusion imaging, or a combination thereof, which may be performed during an invasive surgical procedure, a minimally invasive surgical procedure, a non-invasive surgical procedure, or a combination thereof. Examples of invasive surgical procedures which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems.

Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. In some aspects, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement.

In some aspects, the fluorescence imaging agent(s) used in combination with the methods, systems and kits described herein may be used for targeted imaging, which may be performed during an invasive surgical procedure, a minimally invasive surgical procedure, a non-invasive surgical procedure, or a combination thereof. Targeted imaging refers to imaging agents that may be targeted to preferentially accumulate near, bind to, or be activated by (e.g. have fluorescence activated by) a target tissue type or constituent thereof. The target tissue type may be, for example, tumour tissue, nerve tissue, diseased tissue, or another tissue type.

One or more aspects are directed to a fluorescence imaging agent for use in the imaging systems and methods as described herein. In one or more aspects, the use may comprise vascular blood flow imaging, tissue perfusion imaging, tumour imaging, nerve imaging, diseased tissue imaging or a combination thereof, which may occur during an invasive surgical procedure, a minimally invasive surgical procedure, a non-invasive surgical procedure, or a combination thereof. The fluorescence agent may be included in the kit described herein.

In one or more aspects, the invasive surgical procedure may comprise an oncology surgical procedure, a cardiac-related surgical procedure or a reconstructive surgical procedure. In one or more aspects, the minimally invasive or the non-invasive surgical procedure may comprise a wound care procedure.

At step 104, fluorescence imaging data of the tissue illuminated by the excitation light from an imaging sensor with a color filter array is received. A color filter array can be a mosaic of color filters (e.g., red, green, blue) that overlay the pixels of the imaging sensor. Color filter arrays can be utilized because the typical image sensors detect light intensity with little or no wavelength specificity, and therefore may not separate color information. As such, a color filter array can limit the intensity of light being recorded at the pixel to be associated with the wavelengths transmitted by that color. In other words, the color filter can separate out different color light onto different pixels of the imaging sensor.

In some aspects, the fluorescence imaging data can include at least a first pixel value (i.e., intensity value of a pixel) from the imaging sensor corresponding to a first color of the color filter array and a second pixel value from the sensor corresponding to a second color of the color filter array. The first and second colors of the color filter array can be selected from the group of red, green, and blue. For example, the first color can be red and the second color can be green.

In some aspects, the color filter array can be a Bayer filter. In some aspects, the imaging sensor with a color filter array can be a Bayer-pattern image sensor. In some aspects, the methods or systems include a single Bayer-pattern image sensor. This Bayer-pattern sensor can utilize absorptive filters to separate out blue, green, and red light onto different pixels on the sensor. For example, absorptive dyes can be designed to absorb those parts of the visible spectrum that are not desired for a particular color. In other words, blue pixels can have dyes or a filter overlaid that absorb green and red, green pixels can have dyes or a filter overlaid that absorb blue and red, and red pixels can have dyes or a filter overlaid that absorb blue and green.

Figure 3:
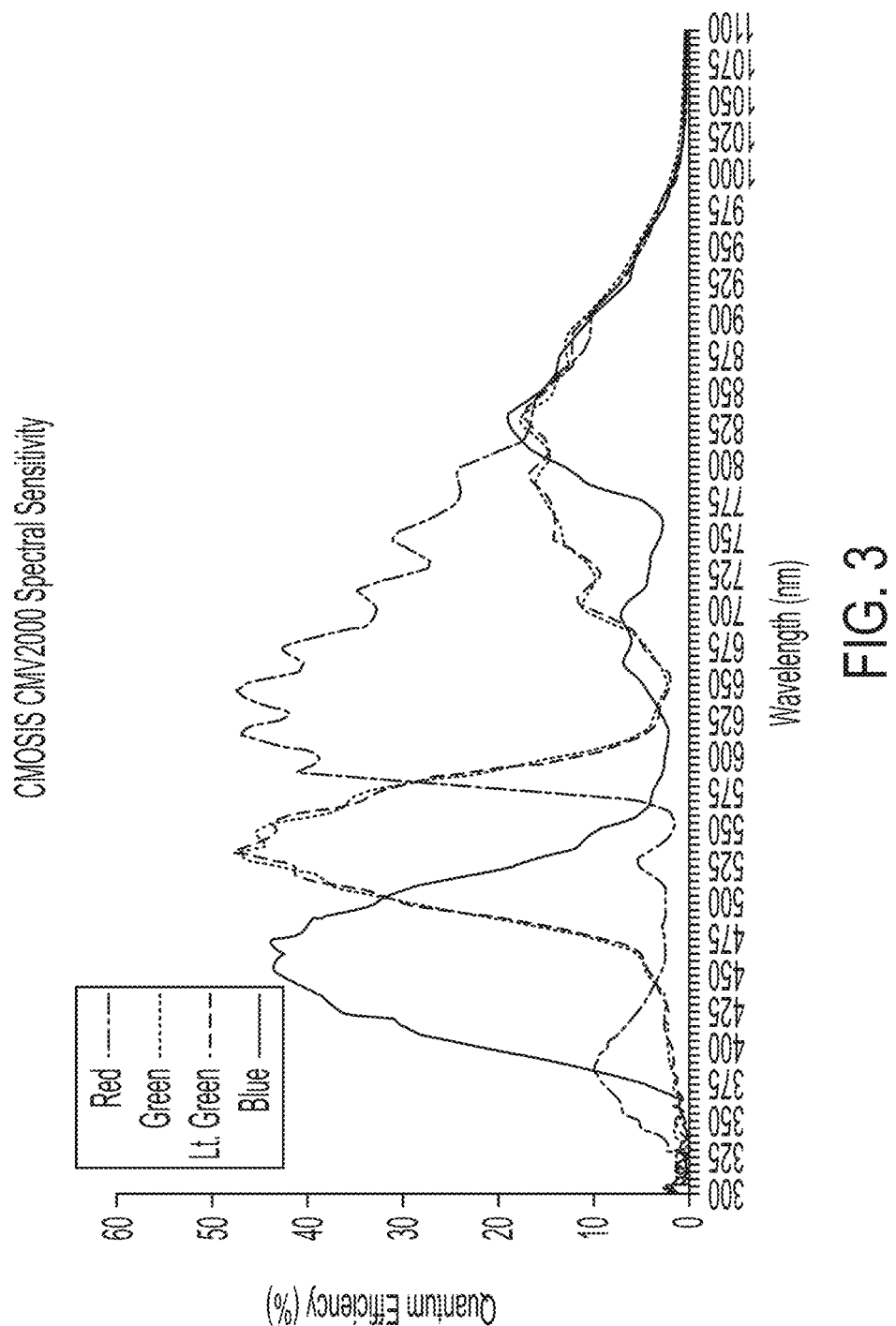
FIG. 3 illustrates the spectral sensitivity for a CMOSIS CMV2000 sensor, according to some examples disclosed herein.

In some aspects, the fluorescence imaging data include near-infrared fluorescence imaging data. In typical visible light imaging applications and in contrast to the fluorescence imaging applications as described herein according to some aspects, there is typically a near-infrared ("NIR") cut filter in front of the imaging sensor. As such, the color filters of the color filter array may not be particularly designed to block NIR and generally all can run clear by about 800 nm. As shown in FIG. 3, the red, green, and blue pixels (i.e., pixels that receive red, green, or blue light) of a CMOSIS CMV2000 sensor are all roughly equally sensitive to NIR illumination beyond 825 nm and their sensitivity curves converge between 650 nm and 800 nm. Note that FIG. 3 shows two green sensitivity curves of slightly different color but with very similar profiles, which correspond to the two green pixels in a typical Bayer pattern of four pixels, and the slight differences shown may reflect measurement variability. The color response for other Bayer-pattern sensors is similar. The method 100 may be performed using an imaging system without a NIR cut filter, so that the NIR sensitivity of the respective color pixels of the color filter array sensor can be exploited to assist with differentiation of the fluorescence imaging data.

In some examples, the intensity values can be associated with the region of the imaged tissue that the fluorescence agent is configured to target. A fluorescence imaging agent can be configured to target a tissue in a number of ways. For example, in some examples, a fluorescence agent is configured to preferentially accumulate in a tissue, such as a tumor, by binding to cells of the tissue. In some examples, the fluorescence agent targets a tissue by activating in the presence of the targeted tissue. So, while the fluorescence agent may be present in non-targeted tissue, the agent fluoresces (or fluoresces more) when in the presence of the targeted tissue and does not fluoresce (or fluoresces less) when in the non-targeted tissue.

Because the received fluorescence imaging data of the tissue illuminated by the excitation light from the imaging sensor with the color filter array includes a contribution from the first fluorescence imaging agent and a contribution from the second fluorescence imaging agent, a clinician may not know what part of the fluorescence imaging data should be attributed to the first fluorescence imaging agent and what part of the fluorescence imaging data should be attributed to the second fluorescence imaging agent.

At step 106, a first contribution to the fluorescence imaging data corresponding to the first fluorescence imaging agent is determined using the first and second pixel values in a first predetermined linear combination. In addition, a second contribution to the fluorescence imaging data corresponding to the second fluorescence imaging agent is determined using the first and second pixel values in a second predetermined linear combination. The first and second predetermined linear combinations can be based on areas under color response curves of the first fluorescence imaging agent for the first and second colors and color response curves of the second fluorescence imaging agent for the first and second colors, and each of the respective imaging agent color response curves can be based on multiplying the respective imaging agent emission profile with a spectral sensitivity of the imaging sensor for the respective color.

For example, a color response curve of the first fluorescence imaging agent for the first color can be based on multiplying the first fluorescence imaging agent emission profile with a spectral sensitivity of the imaging sensor for the first color. A color response curve of the first fluorescence imaging agent for the second color can be based on multiplying the first fluorescence imaging agent emission profile with a spectral sensitivity of the imaging sensor for the second color. A color response curve of the second fluorescence imaging agent for the first color can be based on multiplying the second fluorescence imaging agent emission profile with a spectral sensitivity of the imaging sensor for the first color. Finally, a color response curve of the second fluorescence imaging agent for the second color can be based on multiplying the second fluorescence imaging agent emission profile with a spectral sensitivity of the imaging sensor for the second color.

All of the color response curves can be predetermined before any imaging of the tissue with the first and second fluorescence imaging agent. For example, the fluorescence emission profiles of the first and the second fluorescence emission agent can be measured before any imaging of the tissue with the first and second fluorescence imaging agent. In addition, the spectral sensitivity of the imaging sensor for the respective colors can be measured before any imaging of the tissue with the first and second fluorescence imaging agent. The fluorescence emission profiles of the first and the second fluorescence emission agents as well as the spectral sensitivity of the imaging sensor for the respective color can be stored in a library (e.g., a memory) until their use as described herein. Accordingly, all of the linear combinations can also be predetermined before any imaging of the tissue with the first and second fluorescence imaging agent. Imaging agent emission profiles may vary depending on the imaging agent environment (e.g. blood, water, or tissue type), and accordingly the emission profiles of the first and the second fluorescence agents may be measured, and the corresponding linear combinations predetermined for a variety of surgical environments. In some aspects, method 100 may comprise selecting a surgical environment and retrieving the corresponding predetermined linear combinations for that environment. In some aspects, selecting the surgical environment may be done automatically based on image analysis of an image of the surgical environment acquired by the sensor (e.g., a white light image and/or a fluorescence image).

Figure 4:
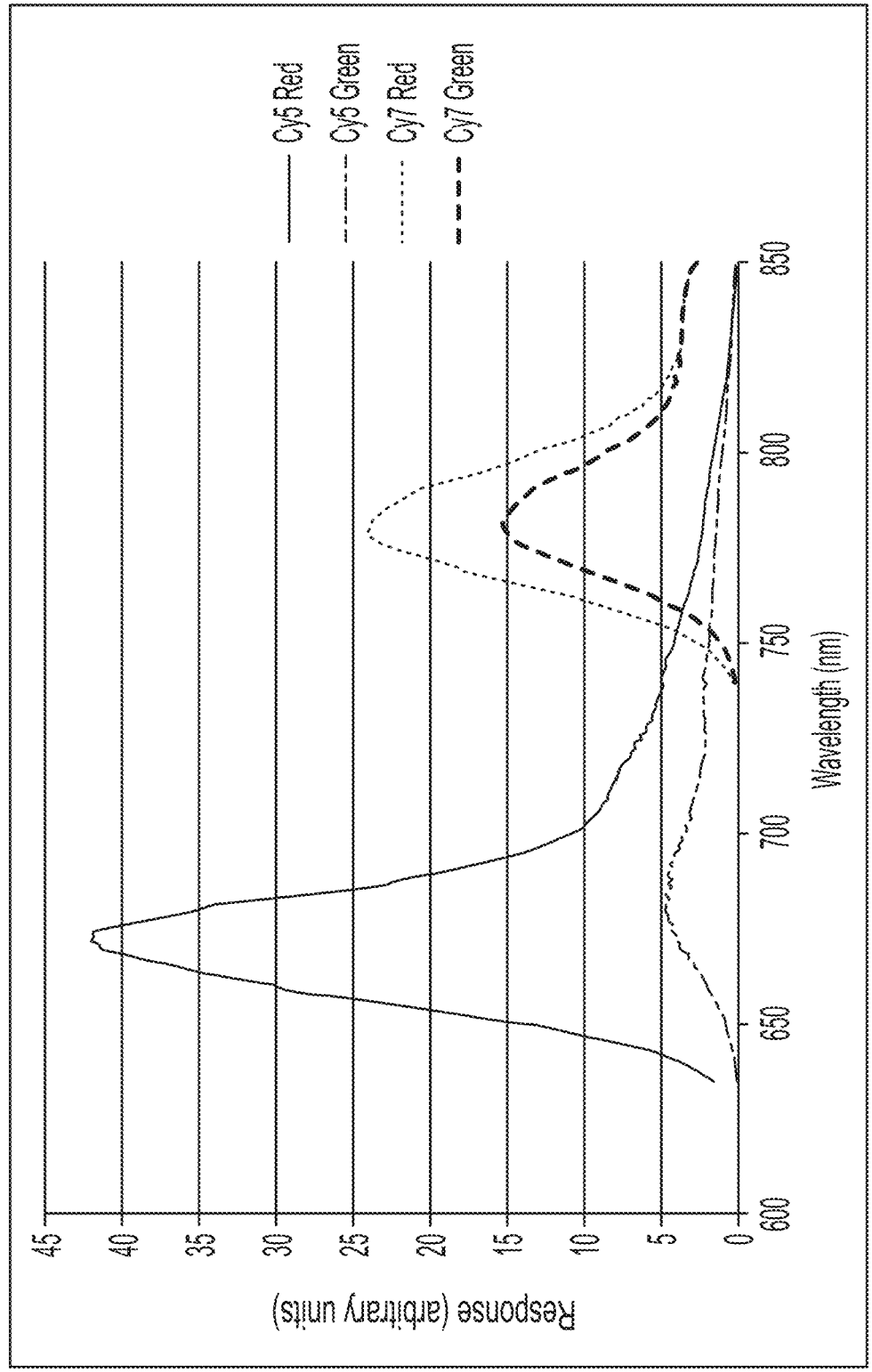
FIG. 4 illustrates the response of red and green pixels to Cy5 and Cy7 by multiplying the product of the fluorescence emission profiles of Cy5 and Cy7 at each wavelength by the spectral sensitivity of CMOSIS CMV200 for red and green at that wavelength, according to some examples disclosed herein.

Using FIGS. 2 and 3, the color response curves of Cy5 and Cy7 for red and green can be determined by the product of Cy5 and Cy7's fluorescence emission at each wavelength (i.e., FIG. 2) and the sensor response (i.e., spectral sensitivity) for that color at that wavelength (FIG. 3). The result of this is shown in FIG. 4 which provides the response of red and green pixels (i.e., pixels receiving red and green light from the filter) to Cy5 and Cy7. Specifically, FIG. 4 provides the response of red and green pixels, respectively, to Cy5 and Cy7 by multiplying the product of the fluorescence emission profiles of Cy5 and Cy7 at each wavelength (FIG. 2) by the spectral sensitivity of CMOSIS CMV200 (FIG. 3) for red and green, respectively, at that wavelength. In FIG. 4, Cy5 Red represents the response of red pixels to Cy5's fluorescence emission at each wavelength, Cy5 Green represents the response of green pixels to Cy5's fluorescence, Cy7 Red represents the response of red pixels to Cy7's fluorescence, and Cy7 Green represents the response of green pixels to Cy7. In other words, FIG. 4 illustrates color response curves of Cy5 and Cy7 for red and green.

As stated above, a first predetermined linear combination and a second predetermined linear combination can determine the first contribution and second contribution to the fluorescence imaging data corresponding to the first and second fluorescence imaging agent. The first and second linear combinations are based on the areas under the color response curves of the first fluorescence imaging agent for the first and second color and the areas under the color response curves of the second fluorescence imaging agent for the first and second colors. The first and second predetermined linear combinations can be stored in a library (e.g., a memory) until they are used for determining a first contribution to the fluorescence imaging data corresponding to the first fluorescence imaging agent and determining a second contribution to the fluorescence imaging data corresponding to the second fluorescence imaging agent. For example, the predetermined first and second linear combinations can be received, utilized, or obtained before or after the methods/systems receive fluorescence imaging data of the tissue illuminated by the excitation light from an imaging sensor with a color filter array (wherein the fluorescence imaging data comprises at least a first pixel value from the sensor corresponding to a first color the color filter array and a second pixel value from the sensor corresponding to a second color of the color filter array).

The areas under the color response curves can be calculated by integrating each color response curve. For example, as shown in FIG. 4, integrating each curve gives (arbitrary units):

$$\Sigma(Cy5\ Red)=1996$$

$$\Sigma(Cy5\ Green)=393$$

$$\Sigma(Cy7\ Red)=1083$$

$$\Sigma(Cy7\ Green)=709$$

From integrating each of the above curves, the total response of red and green pixels, respectively, to any combination of Cy5 and Cy7 in an image can be determined by:

$$Red=1996*Cy5+1083*Cy7$$

$$Green=393*Cy5+709*Cy7$$

The Cy5 and Cy7 in the above equations can refer to the unknown quantities of Cy5 and Cy7 present in the imaged tissue.

Now that there are two equations and two unknowns, Cy5 and Cy7 can be solved for:

$$Cy5=(R-1.53G)/1396$$

$$Cy7=(2.82G-0.55R)/1396$$

The Red (R) and the Green (G) in the above equations can refer to the pixel values from the imaging sensor with the color filter array corresponding to red and green fluorescence light, respectively.

These can hold as long as Cy5 and Cy7 are the only sources of light hitting the sensor, which can be reasonably guaranteed in endoscopic imaging, as the sources of light can be tightly controlled. In some aspects, additional processing can be used to subtract out light such that the only source of light reaching the imaging sensor is fluorescence light from the first and/or second fluorescence imaging agents.

Although the above equations were determined with respect to Cy5 and Cy7 for red and green fluorescence light, the predetermined linear combinations can be determined for any combination of first and second fluorescence imaging agent and an imaging sensor with color filter array. As stated above, a color response curve of the first fluorescence imaging agent for the first color (e.g., curve Cy5 Red shown in FIG. 4) can be based on multiplying the first fluorescence imaging agent emission profile with a spectral sensitivity of the imaging sensor for the first color. The area under the color response curve of the first fluorescence imaging agent for the first color ($A_1$) can then be determined by, for example, integrating the color response curve. A color response curve of the first fluorescence imaging agent for the second color (e.g., curve Cy5 Green shown in FIG. 4) can be based on multiplying the first fluorescence imaging agent emission profile with a spectral sensitivity of the imaging sensor for the second color. The area under the color response curve of the first fluorescence imaging agent for the second color ($A_2$) can then be determined by, for example, integrating the color response curve. A color response curve of the second fluorescence imaging agent for the first color (e.g., curve Cy7 Red shown in FIG. 4) can be based on multiplying the second fluorescence imaging agent emission profile with a spectral sensitivity of the imaging sensor for the first color. The area under the color response curve of the second fluorescence imaging agent for the first color ($A_3$) can then be determined by, for example, integrating the color response curve. A color response curve of the second fluorescence imaging agent for the second color (e.g., curve Cy7 Green shown in FIG. 4) can be based on multiplying the second fluorescence imaging agent emission profile with a spectral sensitivity of the imaging sensor for the second color. The area under the color response curve of the second fluorescence imaging agent for the second color ($A_4$) can then be determined by, for example, integrating the color response curve. Utilizing the areas under the color response curves, the following linear combinations can be prepared to solve for a first contribution to the fluorescence imaging data corresponding to the first fluorescence imaging agent using the first and second pixel values and a second contribution to the fluorescence imaging data corresponding to the second fluorescence imaging agent using the first and second pixel values:

$$F_2 = \frac{A1*C2 - A2*C1}{A1*A4 - A2*A3}; \text{ and}$$

$$F_1 = \frac{C1 - A3*F2}{A1}.$$

In the above equations, $C_1$ can refer to the first pixel value from the imaging sensor corresponding to the first color of the color filter array; $C_2$ can refer to the second pixel value from the imaging sensor corresponding to the second color of the color filter array; $F_1$ can refer to the pixel values from the imaging sensor with the color filter array corresponding to the first and second color fluorescence light that is contributed by the first fluorescence imaging agent (i.e., the first contribution to the fluorescence imaging data corresponding to the first fluorescence imaging agent using the first and second pixel values); and $F_2$ can refer to the pixel values from the imaging sensor with the color filter array corresponding to the first and second color fluorescence light that is contributed by the second fluorescence imaging agent (i.e., the second contribution to the fluorescence imaging data corresponding to the first fluorescence imaging agent using the first and second pixel values).

In some aspects, the imaging sensor can include an intensity value for each pixel (i.e., pixel value) in the imaging sensor. In some aspects, the imaging sensor can include an intensity value for each pixel in the imaging sensor corresponding to each color of the color filter array. In some aspects, a fluorescence image generated by the imaging sensor comprises an intensity value for each pixel in the imaging sensor. In some aspects, the fluorescence image is based on an image generated by the fluorescence imaging sensor. For example, one or more processing steps may be performed between the generation of the fluorescence image by the fluorescence imaging sensor and a fluorescence image based on an image generated by the fluorescence imaging sensor. Examples of such processing steps include scaling, trimming, denoising, and normalizing. Accordingly, in some aspects, the number of intensity values in the fluorescence image based on an image generated by the fluorescence imaging sensor may be different than the number of pixels of the imaging sensor that generated the image from which the received fluorescence image was derived. In addition, generating an enhanced fluorescence image may include one or more of a scaling step, a trimming step, a denoising step, and a normalizing step.

In some examples, the fluorescence image data may be received from an imager or imaging system or may be received from a memory in which a previously generated image is stored. The fluorescence image data can be a video frame or a single image. As used herein, the term fluorescence image/imaging data covers both single images and video frames. In some examples, the method can continuously receive the fluorescence image data over time. For example, the fluorescence image data can be a plurality of video or image frames of the tissue of the subject over time.

In some aspects, the methods and systems can include displaying the fluorescence imaging data, displaying a fluorescence image generated by the imaging sensor, and/or displaying a fluorescence image based on an image generated by the fluorescence imaging sensor. This can also include displaying the first contribution to the fluorescence imaging data corresponding to the first fluorescence imaging agent and/or the second contribution to the fluorescence imaging data corresponding to the second fluorescence imaging agent. In addition, the methods and systems can include displaying a fluorescence image generated by the first contribution and/or second contribution to the fluorescence imaging data or displaying a fluorescence image based on an image generated by the first contribution and/or second contribution to the fluorescence imaging data.

In some aspects, the first contribution and/or second contribution to the fluorescence imaging data can be displayed using distinct color maps. In some aspects, a fluorescence image generated by the first contribution and/or second contribution to the fluorescence imaging data or a fluorescence image based on an image generated by the first contribution and/or second contribution to the fluorescence imaging data can be displayed using distinct color maps. The color maps can be gray-scale color maps or color spectrum color maps. The color maps may be displayed as an overlay on visible light images. The color maps may be updated as new fluorescence imaging data is generated and/or received.

The methods and processes described herein may be performed by code or instructions to be executed by a computer, processor, manager, or controller, or in hardware or other circuitry. Because the algorithms that form the basis of the methods (or operations of the computer, processor, or controller) are described in detail, the code or instructions for implementing the operations of the method aspects may transform the computer, processor, or controller into a special-purpose processor for performing the methods described herein.

Also, another aspect may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, or controller which is to execute the code or instructions for performing the method aspects described herein.

Figure 5:
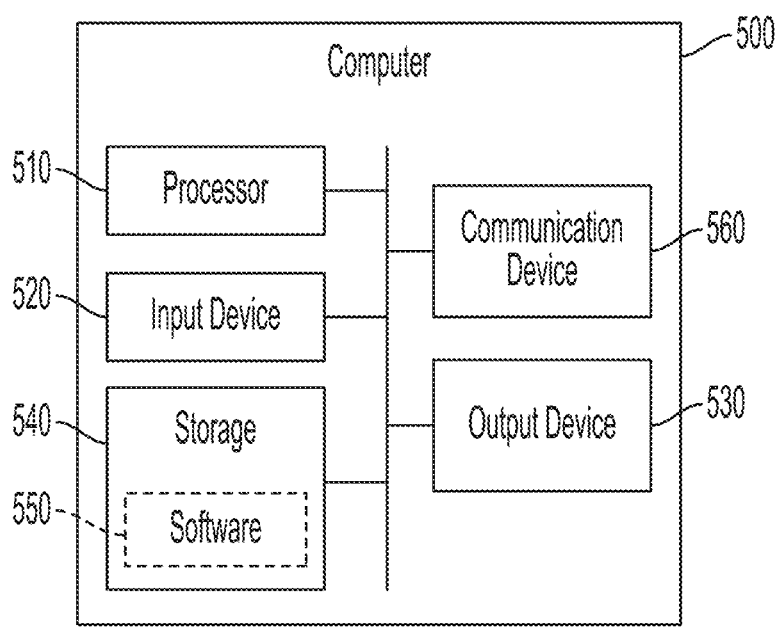
FIG. 5 depicts a computer, in accordance with some examples disclosed herein.

FIG. 5 illustrates a computer, in accordance with some examples. Computer 500 can be a component of a system or method for distinguishing between fluorescence imaging data contributions corresponding to two fluorescence imaging agents in a tissue of a patient during surgical imaging, such as method 100. In some examples, computer 500 may be configured to execute a method for distinguishing between fluorescence imaging data contributions corresponding to two fluorescence imaging agents in a tissue of a patient during surgical imaging, such as all or part of method 100 described above with respect to FIG. 1.

Computer 500 can be a host computer connected to a network. Computer 500 can be a client computer or a server. As shown in FIG. 5, computer 500 can be any suitable type of microprocessor-based device, such as a personal computer; workstation; server; or handheld computing device, such as a phone or tablet. The computer can include, for example, one or more of processor 510, input device 520, output device 530, storage 540, and communication device 560.

Input device 520 can be any suitable device that provides input, such as a touch screen or monitor, keyboard, mouse, or voice-recognition device. Output device 530 can be any suitable device that provides output, such as a touch screen, monitor, printer, disk drive, or speaker.

Storage 540 can be any suitable device that provides storage, such as an electrical, magnetic, or optical memory, including a RAM, cache, hard drive, CD-ROM drive, tape drive, or removable storage disk. Communication device 560 can include any suitable device capable of transmitting and receiving signals over a network, such as a network interface chip or card. The components of the computer can be connected in any suitable manner, such as via a physical bus or wirelessly. Storage 540 can be a non-transitory computer-readable storage medium comprising one or more programs, which, when executed by one or more processors, such as processor 510, cause the one or more processors to execute methods described herein, such as all or part of method 100 described above with respect to FIG. 1.

Software 550, which can be stored in storage 540 and executed by processor 510, can include, for example, the programming that embodies the functionality of the present disclosure (e.g., as embodied in the systems, computers, servers, and/or devices as described above). In some examples, software 550 can be implemented and executed on a combination of servers such as application servers and database servers.

Software 550 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 540, that can contain or store programming for use by or in connection with an instruction execution system, apparatus, or device.

Software 550 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 500 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 500 can implement any operating system suitable for operating on the network. Software 550 can be written in any suitable programming language, such as C, C++, Java, or Python. In various examples, application software embodying the functionality of the present disclosure can be deployed in different configurations, such as in a client/server arrangement or through a Web browser as a Web-based application or Web service, for example.

The methods and processes described herein may be performed by code or instructions to be executed by a computer, processor, manager, or controller, or in hardware or other circuitry. Because the algorithms that form the basis of the methods (or operations of the computer, processor, or controller) are described in detail, the code or instructions for implementing the operations of the method examples may transform the computer, processor, or controller into a special-purpose processor for performing the methods described herein.

Also, another aspect may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, or controller which is to execute the code or instructions for performing the method examples described herein.

For the purpose of clarity and a concise description, features are described herein as part of the same or separate aspects or examples; however, it will be appreciated that the scope of the disclosure includes aspects or examples having combinations of all or some of the features described.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X". In addition, reference to phrases "less than", "greater than", "at most", "at least", "less than or equal to", "greater than or equal to", or other similar phrases followed by a string of values or parameters is meant to apply the phrase to each value or parameter in the string of values or parameters.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "providing," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some aspects also relates to a device for performing the operations herein. This device may specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMS, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each connected to a computer system bus. Furthermore, the computing systems referred to in the specification may include a single processor may be architectures employing multiple processor designs, such as for performing different functions or for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The structure for a variety of these systems can appear from the description above. In addition, the present disclosure is not described with reference to any particular programming language. It will be appreciated that a variety of programming languages may be used to implement the teachings of the present invention as described herein.

A kit may include any part of the systems described herein, and/or the tangible non-transitory computer-readable medium described above having computer-executable (readable) program code embedded thereon that may provide instructions for causing one or more processors, when executing the instructions, to perform one or more of the methods described herein. For instance, the instructions may cause one or more processors, when executing the instructions, to illuminate tissue with excitation light to simultaneously excite both a first fluorescence imaging agent and a second fluorescence imaging agent in the tissue, wherein the first and second fluorescence imaging agents have different fluorescence emission profiles in the tissue; receive fluorescence imaging data of the tissue illuminated by the excitation light from an imaging sensor with a color filter array, wherein the fluorescence imaging data comprises at least a first pixel value from the sensor corresponding to a first color of the color filter array and a second pixel value from the sensor corresponding to a second color of the color filter array; determine a first contribution to the fluorescence imaging data corresponding to the first fluorescence imaging agent using the first and second pixel values in a first predetermined linear combination; and determine a second contribution to the fluorescence imaging data corresponding to the second fluorescence imaging agent using the first and second pixel values in a second predetermined linear combination, wherein the first and second predetermined linear combinations are based on areas under color response curves of the first fluorescence imaging agent for the first and second colors and color response curves of the second fluorescence imaging agent for the first and second colors, and each of the respective imaging agent color response curves are based on multiplying the respective imaging agent emission profile with a spectral sensitivity of the imaging sensor for the respective color. Furthermore, the kit may include instructions for use of at least some of its components (e.g., for installing the computer-executable (readable) program code with instructions embedded thereon, etc.). In some aspects, a kit may include any part of the systems described herein and a fluorescence imaging agent(s) such as those described above.

One or more aspects are directed to a fluorescence imaging agent(s) for use in the imaging systems and methods as described herein. In one or more aspects, the use may comprise blood flow imaging, tissue perfusion imaging, lymphatic imaging, or a combination thereof, which may occur during an invasive surgical procedure, a minimally invasive surgical procedure, a non-invasive surgical procedure, or a combination thereof. The fluorescence agent(s) may be included in the kit described herein. In one or more aspects, the minimally invasive or the non-invasive surgical procedure may comprise a wound care procedure.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method of distinguishing between fluorescence imaging data contributions corresponding to a first fluorescence imaging agent and a second fluorescence imaging agent in a tissue of a patient during surgical imaging, comprising:
    illuminating the tissue with excitation light to simultaneously excite both the first fluorescence imaging agent and the second fluorescence imaging agent in the tissue, wherein the first and second fluorescence imaging agents have different fluorescence emission profiles in the tissue;
    receiving fluorescence imaging data of the tissue illuminated by the excitation light from an imaging sensor with a color filter array, wherein the fluorescence imaging data comprises at least a first pixel value from the imaging sensor corresponding to a first color of the color filter array and a second pixel value from the imaging sensor corresponding to a second color of the color filter array;
    determining color response curves of the first fluorescence imaging agent for the first and second colors and color response curves of the second fluorescence imaging agent for the first and second colors based on multiplying the respective fluorescence imaging agent emission profile with a spectral sensitivity of the imaging sensor for each respective color;
    determining areas under the color response curves of the first fluorescence imaging agent for the first and second colors and the color response curves of the second fluorescence imaging agent for the first and second colors;
    determining a first contribution to the fluorescence imaging data corresponding to the first fluorescence imaging agent using the first and second pixel values in a first predetermined linear combination; and
    determining a second contribution to the fluorescence imaging data corresponding to the second fluorescence imaging agent using the first and second pixel values in a second predetermined linear combination,
    wherein the first and second predetermined linear combinations are based on the areas under the color response curves.

2. The method of claim 1, wherein the color filter array comprises a Bayer filter.

3. The method of claim 1, wherein the fluorescence imaging data comprises near-infrared fluorescence imaging data.

4. The method of claim 1, wherein the first and second colors of the color filter array are two selected from the group of red, green, and blue.

5. The method of claim 4, wherein the first color is red and the second color is green.

6. The method of claim 1, wherein the first fluorescence imaging agent is Cy5 and the second fluorescence imaging agent is Cy7.

7. The method of claim 1, further comprising displaying the fluorescence imaging data.

8. The method of claim 1, further comprising displaying the first contribution to the fluorescence imaging data corresponding to the first fluorescence imaging agent and/or the second contribution to the fluorescence imaging data corresponding to the second fluorescence imaging agent.

9. The method of claim 8, wherein the first contribution and/or the second contribution are displayed using distinct color maps.

10. The method of claim 1, further comprising subtracting out light such that the only source of light reaching the imaging sensor is fluorescence light from the first and/or second fluorescence imaging agent.

\* \* \* \* \*